United States Patent [19]

Dochniak

[11] Patent Number: 5,496,907
[45] Date of Patent: Mar. 5, 1996

[54] WET ADHESION MONOMERS WITH UREIDO FUNCTIONALITY AND POLYMERS PREPARED THEREFROM

[75] Inventor: Michael J. Dochniak, Stillwater, Minn.

[73] Assignee: H. B. Fuller Licensing & Financing, Inc., Wilmington, Del.

[21] Appl. No.: 300,309

[22] Filed: Sep. 2, 1994

Related U.S. Application Data

[63] Continuation-in-part of Ser. No. 25,091, Mar. 2, 1993, Pat. No. 5,399,706.

[51] Int. Cl.[6] .................................... C08G 18/62
[52] U.S. Cl. ............... 528/73; 252/182.18; 548/324.1; 548/324.5; 528/75; 528/341; 528/393; 526/263
[58] Field of Search .............. 252/182.18; 548/324.1, 548/324.5; 528/73, 75, 341, 393; 526/263

[56] References Cited

U.S. PATENT DOCUMENTS

| | | | |
|---|---|---|---|
| 2,613,212 | 10/1952 | Hurwitz et al. | 548/313.7 |
| 3,300,429 | 1/1967 | Glavis et al. | 524/516 |
| 3,919,233 | 11/1975 | Rebling et al. | 544/370 |
| 4,302,375 | 11/1981 | Dixon et al. | 524/555 |
| 4,340,743 | 6/1982 | Sandri et al. | 548/318 |
| 4,429,095 | 1/1984 | Sandri et al. | 526/263 |
| 4,783,539 | 11/1988 | Abboud et al. | 548/320 |
| 4,883,854 | 11/1989 | Coury et al. | 528/28 |
| 4,883,873 | 11/1989 | Abboud et al. | 544/316 |
| 5,138,016 | 8/1992 | Murdock et al. | 528/55 |
| 5,399,706 | 3/1995 | Dochniak | 548/324.1 |

FOREIGN PATENT DOCUMENTS

| | | |
|---|---|---|
| 2829198 | 1/1979 | Germany . |
| 689705 | 4/1953 | United Kingdom . |
| 91/12243 | 8/1991 | WIPO . |

OTHER PUBLICATIONS

"Non–Voc Modifier To Improve The Gloss Of Water–Borne Coatings", Fred Giles, Jr., Presented at *Water–Borne & Higher–Solids Coatings Symposium*, New Orleans, La., Feb. 6–8, 1991.

*Chem. Abst.,* File CA record for DE 2150438 and File Registry record for 2–Imidazolidinone, 1–[2–[(2–aminoethlyl)amino]ethyl]–3–methyl–. Jun., 1978.

Israel, et al, *J. Med. Chem.,* 14, 1042–1047, (1971).

Primary Examiner—James J. Seidleck
Assistant Examiner—R. F. Johnson
Attorney, Agent, or Firm—Vidas, Arrett & Steinkraus

[57] ABSTRACT

Compounds containing a ureido group which are useful in preparing dispersions of polymers having good wet adhesion properties and low volatility. Compounds having the formula:

$$NC-CH_2-CH(R^1)-N(A)-R^2-N\underset{\underset{}{\diagdown\diagup}}{\overset{}{\diagup}}\overset{O}{\underset{}{\diagdown}}NH$$

where $R^1$ is H or an alkyl group, $R^2$ is alkylene optionally interrupted with one or more ether oxygen atoms and A is H or a residue of an active hydrogen reactive compound are useful for incorporating ureido and optionally nitrile functionality into polymers and as precursors to amino compounds prepared by reduction of the nitrile group thereof. Compounds having the formula:

$$HN(B)-CH_2-CH_2-CH(R^1)-N(A)-R^2-N\underset{\underset{}{\diagdown\diagup}}{\overset{}{\diagup}}\overset{O}{\underset{}{\diagdown}}NH$$

where B is defined as for A and the same or different than A are also disclosed. The disclosed compounds have use as chain extending or terminating monomers for polyurethane dispersions when one or both of A and B are H and, when one of A and has ethylenic unsaturation, as wet adhesion monomers in dispersions of free radically polymerized polymers of unsaturated monomers.

7 Claims, No Drawings

WET ADHESION MONOMERS WITH UREIDO FUNCTIONALITY AND POLYMERS PREPARED THEREFROM

CROSS-REFERENCE TO RELATED APPLICATION

The present application is a continuation-in-part of Ser. No. 25,011, filed Mar. 2, 1993, now U.S. Pat. No. 5,399,706, issued Mar. 21, 1995.

BACKGROUND OF THE INVENTION

Ethylenically unsaturated compounds having imidazolidinone groups thereon which provide ureido hydrogen functionality are known as good wet adhesion monomers. References describing such compounds include: U.S. Pat. Nos. 4,302,375; 4,340,743; 4,319,032; 4,429,095; 4,632,957; 4,783,539; 4,880,931; and 4,882,873. In some disclosed structures a cyano group may also be present.

Gilles, Jr., et al, "Non-VOC Modifier To Improve The Gloss Of Water-Borne Coatings". presented at the Waterborne & High solids Coating Symposium (Feb. 6–8, 1991), 268–278, U. So. Miss. Dep of Poly. Sci.; U.S. Pat. No. 2,613,212; DE 2,829,198; and WO 91/12243 disclose various imidazolidinone compounds with hydroxy functional ureido groups and their physical properties as additives and reactants.

Israel, Modest, *J. Med. Chem.*, 14<1971>, 1042,1047, CODEN JMCMAR, describes a diamine compound containing a ureido hydrogen as an intermediate in the formation of a polyamine. The polyamine's growth-inhibitory activity was tested against KB cells (buman epidermoid carcinoma). The diamine intermediate compound has the formula:

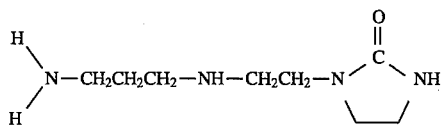

In U.S. Pat. No. 3,919,233 certain imidazolidinone diamine compounds are reported as intermediates for the synthesis of antiviral compounds. Such imidazolidinone diamine compounds, however, do not have a ureido hydrogen atom on the imidazolidionone ring.

SUMMARY OF THE INVENTION

The present invention pertains to the the synthesis, purification, and physical properties of novel compounds containing a ureido group which are useful in preparing dispersions of polymers having good wet adhesion properties.

The invention in one aspect pertains to nitrile compounds useful for incorporating ureido and optionally nitrile functionality into polymers, the compounds having the formula:

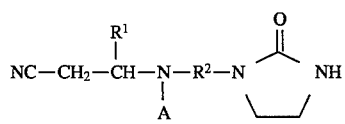

where $R^1$ is H or an alkyl group, $R^2$ is alkylene optionally interrupted with one or more ether oxygen atoms and A is H or a residue of an active hydrogen reactive compound.

A further aspect of the invention are primary amino compounds prepared by reduction of the nitrile group in formula II and derivatives thereof. Such compounds have the formula:

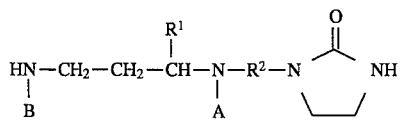

where B is defined as for A and the sane or different than A.

The compounds of the invention have low volatility and provide numerous options for incorporating ureido hydrogen functionality into a wide variety of polymers. Polymers and polymer dispersions prepared from the nitrile or amine compounds of the invention are further aspects of the present invention.

Especially preferred compounds of the invention are those in which at least one of A or B are H, or at least one of A and B include free radically polymerizable ethylenic unsaturation. The novel compounds of the invention are subject to the following provisos: in formula II when $R^1$ is H, A is a residue of an active hydrogen reactive compound which is an unsaturated isocyanate, an unsaturated anhydride, or an active hydrogen reactive compound which does not contain ethylenic unsaturation; in formula III when $R^1$ is H, A and B are not both H.

DETAILED DESCRIPTION OF THE INVENTION

The compounds of the invention all include a ureido hydrogen atom on the imidazolidinone ring. The ureido hydrogen atom on the imidazolidinone group contributes to improved adhesion properties obtained with polymers of the invention and also provides a site for melamine crosslinking to improve heat and solvent resistance properties of polymers formed from the compounds of the invention.

Compounds of formula II where A is Hydrogen are produced by cyanoalkylation of aminoalkyleneethyleneurea or aminoalkyleneoxyalkyleneethyleneurea compound of the formula:

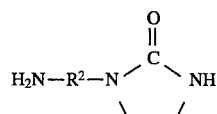

using acrylonitrile, 2-butenenitrile or higher 2-alkenenitriles. Particularily preferred are the compounds derived from 2-butenenitrile or 2-pentenenitrile, i.e., compounds of formula II where A is H and $R^1$ is methyl or ethyl, respectively. Other higher 2-alkenenitriles, however may also be used, in particular up to about $C_{20}$.

The group $R^2$ is an alkylene or alkylene interrupted with one or more ether oxygen atoms. The alkylene group may be linear, branched or cyclic. Suitably $R^2$ is a $C_1$–$C_{20}$ alkylene or alkyleneoxyalkylene group, more preferably $C_2$–$C_6$. A suitable example of an alkylene group interrupted with one or more ether oxygen atoms is alkyleneoxyalkylene, such as propyleneoxyethylene which may be provided as described in Example 10 below.

Cyanoalkylation procedures are well known in the art. A representative literature example is Bruson "Cyanoethylation", *Organic Reactions*, Volume V, edited by R. Adams, John Wiley and Sons, Inc., New York, 1949. Commercial cyanoalkylation service is offered by Tomah Products Co., Milton, Wis. and by Nova Molecular Technologies, Inc., Janesville, Wis. The products of the cyanoalkylation reaction are nitrile adduct compounds of the formula:

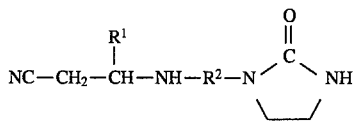   VI where $R^1$ and $R^2$ are as previously defined.

Nitrile compounds as in formula VI, where $R^1$ is alkyl, are novel compounds of the invention. Such compounds provide advantageous chemical and physical properties compared to similar compounds where $R^1$ is H. Such compounds may be incorporated into polymer structures by reaction of the secondary amino group, for instance by reaction with compounds having plural isocyanate or plural epoxy groups thereon.

Further novel nitrile compounds of the invention are compounds of the formula II where A is:

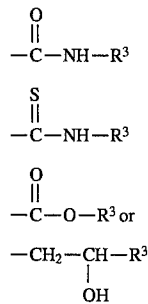

where $R^3$ is alkyl, suitably $C_2$–$C_{20}$ alkyl, optionally substituted with a hydroxyl or alkoxyl group. The alkyl group may be linear, branched or cyclic. Reduction of the cyano group of such compounds yields a compound within the scope of formula III where A is a group of formulas V–VIII and B is H. Such compounds are primary amines which can be utilized in the synthesis of polyurethane/urea or epoxy/amine adduct polymers.

Nitrile compounds of formula II may be incorporated directly into polymers by reaction of active hydrogen atoms present on the nitrile molecule, i.e. when A=H or when A contains a hydroxyl group. Alternatively, as noted above, the nitrile compound may be reduced to an amine.

Reduction of these nitrile compounds, using reagents such as alkali borohydrides, $H_2$/Raney nickel, etc., also follows procedures well known in the literature and can be obtained as a contract service by the same companies. An example of a literature reduction is found in Winas, U.S. Pat. No. 2,334,140 (1943); Chem. Abst., 38, 2666 (1944).

Amine compounds of the invention are provided when one or both of A or B in formulas II or ! II is hydrogen. When both A and B are H and $R^1$ is alkyl, especially ethyl or higher, the secondary amino site is sufficiently less reactive than the primary amine site that selective reaction at the primary amine is easily accomplished.

Selective substitution at the secondary amine site is possible as well, by reacting that site after formation of the nitrile but prior to reduction of the nitrile group to form the primary amine. Thus it is possible to obtain substitution, at either site. When reaction at both amine sites is desired with different reactive compounds, it is also feasible, when $R^1$ is alkyl, to react first the primary amine with one reactive compound and then the secondary amine with the second reactive compound.

The amine compounds of the invention may be reacted in any conventional reaction of amines in polymer formation.

Particular reactions within the scope of the invention are reactions with active hydrogen reactive compounds such as isocyanates, isothiocyanates, epoxies, carbonates, carboxylic or sulfonic acids, anhydrides, chloroformates, esters and alkyl halides.

Chain extended polymers produced from diamine compounds of formula III where A and B are H are characterized by the presence of a plurality of groups of the formula:

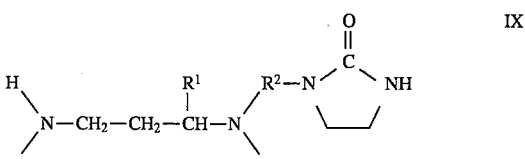   IX where $R^1$ and $R^2$ are as previously defined. Such polymers are also characterized by the absence of imidazolidinone groups which do not contain ureido hydrogen.

Monoamine compounds of the invention can be usefully employed as chain terminating agents in polyurethanes or epoxy/amine adduct polymers.

The nitrile or amine compounds of the invention may alternatively be reacted to prepare radically polymerizable ethylenically unsaturated monomer and prepolymer compounds having pendant imidazolidinone functionality. Such compounds may be prepared by reaction of an ethylenically unsaturated active hydrogen compound, such as an unsaturated acid, isocyanate, isothiocyanate, ester, or epoxy compound, with a compound of formula II or III where at least one of A or B is H. Suitable examples of ethylenically unsaturated active hydrogen reactive compounds include, for instance, acrylic and methacrylic acids and their anhydrides or acid chlorides, isocyanatoethyl methacrylate, isocyanatoethyl acrylate, glycidyl acrylate, glycidyl methacrylate, vinyl glycidyl ether and a mono-, di-, or triisocyanate of the formula:

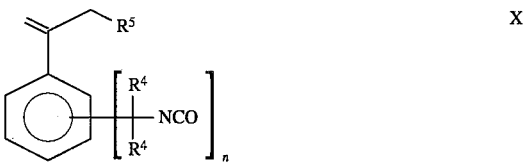   X where each $R^4$ is independently a $C_{1-6}$ alkyl, $R^5$ is H or $R^4$ and n is 1–3.

An alternative method of preparing ethylenically unsaturated imidazolidinone compounds within the scope of the invention is to react a plural isocyanate or epoxy functional compound with both an ethylenically unsaturated compound having an active hydrogen functional group, and an imidazolidinone compound of the formula III where at least one of A or B is H. Suitable examples of ethylenically unsaturated compounds having active hydrogen groups include allyl alcohol, allyl amine, acrylic acid, hydroxyethyl acrylate, hydroxypropyl acrylate, diethylene glycol monoacrylate, triethylene glycol monoacrylate, polyethylene glycol monoacrylate, hydroxyethyl methacrylate, hydroxypropyl methacrylate, diethylene glycol monomethacrylate, triethylene glycol monomethacrylate, polyethylene glycol monomethacrylate, crotonic acid, itaconic acid, maleic acid, fumaric acid and half esters of maleic and fumaric acids.

Particularly preferred are compounds of formula III in which one of A or B, most preferably B, is the residue of an ethylenically unsaturated isocyanate, carboxylic acid or epoxy compound and the other of A or B, most preferably A, is the residue of an alkyl isocyanate (i.e. a residue as in formula V). Such compounds comprise two branched sites:

of ureido hydrogen atoms as well as ethylenic unsaturation for incorporation into free radically polymerized polymer structures.

The compounds of the invention provide numerous advantageous properties to polymers into which they become incorporated. The pendant or terminal ureido hydrogen atom provided with the imidazolidinone functional group enhances polarity, improving adhesion of many polymer products of the invention. In the case of diamine compounds, by providing the imidazolidinone group on a chain extending monomer, polymer molecular weight can be built up while assuring extensive distribution of the imidazolidinone group throughout the polymer network. In reactions with isocyanates, the amine compounds of the invention provide urea linkages having improved chemical resistance over carbamate linkages, as well as better internal polymer strength and heat resistance due to hydrogen bonding.

Non-volatile, water soluble diamines containing a ureido hydrogen have shown unexpected properties. Compared to similar low molecular weight, water soluble diamines the compounds of the invention exhibit extremely low vapor pressures. Reduced vapor pressures lower VOC and helps eliminate hazards through inhalation.

The invention is illustrated by the following non-limiting examples.

EXAMPLE 1

2-Aminoethylethylene urea, corresponding to the formula

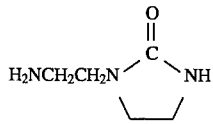

50 gm (.387 Eq), was dissolved in 100 ml isopropyl alcohol and heated to reflux. 2-pentenenitrile 34.53 gm (0.425 Eq) was slowly added over a 2 hour period keeping the reaction mixture at reflux. This cyanoalkylation reaction forms the product diagramed below.

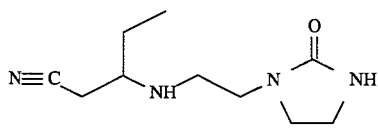

EXAMPLE 2

The solution containing the product of example 1 is cooled to 10° C. and 22.08 gm (0.387 Eq) methyl isocyanate is slowly added keeping the reaction temperature around 10° C. The product formed is diagramed below.

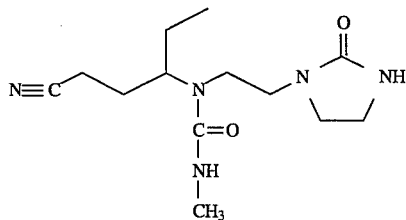

EXAMPLE 3

To the reaction mixture from example 2 is charged an initial nickle metal catalyst, ammonia, and hydrogen gas then heated to 100° C. at 70 atm for approximately 4 hours. Solvent is stripped off. The resulting product is diagramed below.

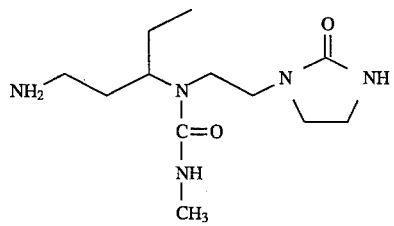

EXAMPLE 4

The amine product of Example 3 is dissolved in 100 gm (5.5 moles) de-ionized water. To this is slowly added 25.05 gm (0.403 Eq) 96% active methacrylic anhydride and 2,000 ppm hydroquinone to form a compound:

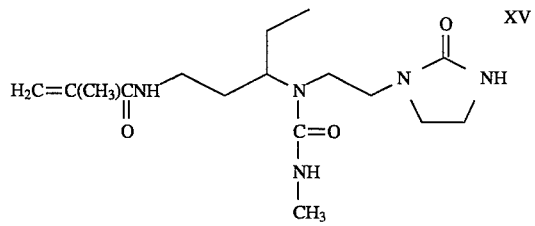

EXAMPLE 5

To a reaction flask was charged 250 gm (3.46 moles) 2-butanone and 88.2 gm (0.42 Eq) of the cyanoalkylation product of Example 1. The solution was heated to 50° C. and 125.8 gm (0.42 Eq) octadecyl isocyanate was slowly added over a 15 minute period and heated an additional 15 minutes. The solution was cooled to room temperature and the precipitate was filtered. The white solid has a melting point of 94°–96° C. The nitrile was reduced as described in example 3 and the resulting product was reacted with m-TMI, i.e. (benzene, 1-(1-isocyanato-1-methyl ethyl)-3-(1-methyl ethenyl)), to form a compound:

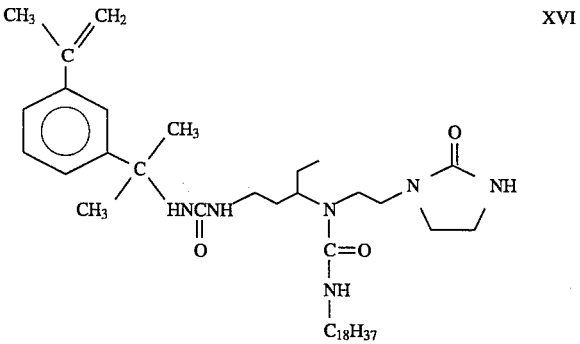

EXAMPLE 6

2-Aminoethyl ethylene urea was disolved in water and heated to 100° C. 2-pentenenitrile was slowly added over a 2 hour period keeping the reaction mixture around 100° C. The product, a nitrile as produced in Example 1, was not isolated. To the reaction mixture was charged an initial metal catalyst, ammonia, and hydrogen gas then heated to 100° C. at 70 atm for approximately 4 hours. The resulting product was analyzed by GC/MS to give a composition described below.

| Compound | Weight % |
| --- | --- |
| Amyl amines | 6.53 |
| 1,3-Diaminopentane | 1.46 |
| 2-aminoethyleneurea | 0.566 |
| Unknowns | 0.6616 |
| Desired product | 80.47 |
| Water | 10.3 |

The reaction product was purified by short path distillation. The unit was a two stage glass distact still from UIC Inc. The first stage was run at a relatively low vacuum (60 mmHg) and temperature (140° C.) to remove low boilers (Amyl amines, 1,3 diaminopentane, 2-aminoethyl ethylene urea, and water). The second stage was run with a low vacuum (0.1 mm Hg) and decreased temperatures (110° C.) to separate the desired product from high boilers (unknowns). The process recovered 87% of the desired product. The sample, a clear, colorless, semi-viscous liquid, was characterized by carbon 13 and amine titration. The carbon-13 NMR spectra of the sample dissolved in deuterated chloroform indicated a purity level very high, nearly 100%. The measured amine number of 522 mg KOH/g material yields an approximate diamine content of 98% corresponding to the formula:

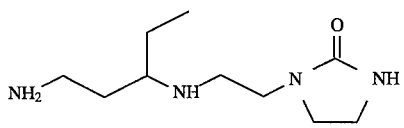

XVII

The physical properties of this diamine are described below:
Molecular weight=214 grams/tool
Purity=Greater than 98%
Appearance/odor=Clear liquid/odorless
Gardner color=Less than 1
Viscosity=800 centipoise
Solubility in water=Complete
Aqueous surface tension=57.85 dynes/cm
pKb's at 25° C.=3.8 and 6.5
ph of 1% solution=10.25
Flash point (ASTM D-93)=>450° F.
Boiling point =160° C. at .05 torr
Vapor pressure=0.000004 torr at 25° C.
Volatilization=Non-volatile
(Federal Test Method #24)

The list below compares several water soluble, liquid diamines and their vapor pressures.

| Diamine | Vapor Pressure |
| --- | --- |
| Ethylene Diamine (60.10 g/mol) | 10.0 torr at 25° C. |
| 1,3-diaminopentane (102 g/mol) | 3.5 torr at 25° C. |
| m-Xylylene diamine (136 g/mol) | 0.1 torr at 25° C. |
| Diamine of formula XVII (214 g/mol) | 0.000004 torr at 25° C. |

EXAMPLE 7

To a reaction flask was charged 68 gm (0.310 moles) of the diamine for formula XVII, 70 gm (0.97 Moles) 2 butanone. This mixture was cooled to 0° C. and 62.50 gm (0.310 moles) m-TMI, was slowly added keeping the reaction temperature between 0°–5° C. After evaporating off solvent the material was analyzed using carbon 13 NMR. The sample, a clear, colorless, viscous liquid had a composition described below.

| Species | Relative Intensity |
| --- | --- |
| m-TMI/primary amine | 0.775 |
| m-TMI/secondary amine | 0.107 |
| Unreacted diamine | 0.118 |

The results indicate a majority of the product formed corresponds to the structure:

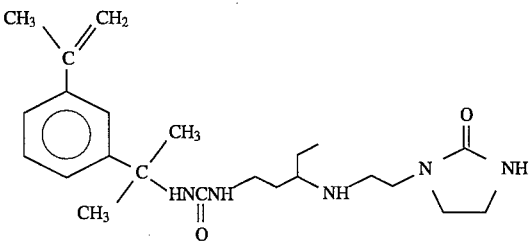

XVIII

EXAMPLE 8

44.6 gm (0.208 moles) of the diamine diagramed below

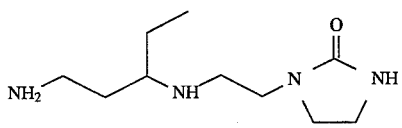

XVII was dissolved in 34 gm (1.9 moles) de-ionized water containing 2,000ppm hydroquinone. To this solution was slowly added 32.09 gm (0.208 Moles) of methacrylic anhydride keeping the temperature below 60° C. The sample, a clear, colorless, semi-viscous liquid, was dissolved in deuterated water and analyzed by Carbon 13 NMR. Interpretation of this spectrum detected no unreacted diamine and the methacrylic anhydride reacts exclusively with the primary amine to form the compound:

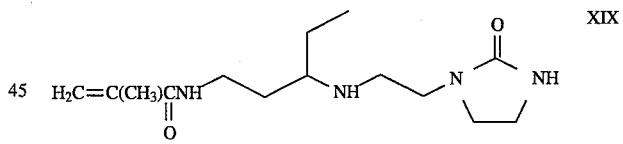

XIX

EXAMPLE 9

2-aminoethyl ethylene urea is cyanopropylated with 2-butenenitrile in the manner of example 6 to provide a nitrile compound of the formula:

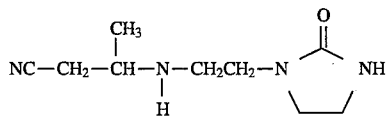

XX

The nitrile is then reduced, also in the manner of example 6, to provide a diamine having the formula:

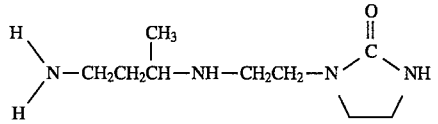

XXI

EXAMPLE 10

Hydroxyethylethyleneurea was cyanoethylated with acrylonitrile and then reduced in a process similar to Example 6 to produce a monoamine of the formula:

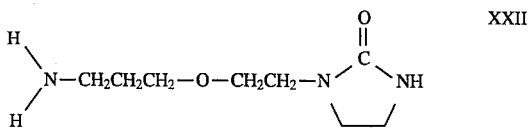
XXII

This monoamine when cyanobutylated and reduced as in Example 6 will provide a diamine of the invention having the formula:

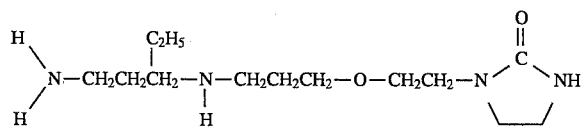

POLYMER PREPARATION EXAMPLES

EXAMPLE 11

Non-ionic Polyurethane/urea Dispersion

To a reaction flask was charged 65.3 gm (.1306 Eq) polyethylene glycol, 25.81 gm (.2325 Eq) isophorone diisocyanate and two drops of Metacure™ T-12 dibutyl tin dilaurate. This mixture was heated for 3 hours at 90° C. using overhead stirring. When the isocyanate content reached approximately 4.7% one hundred grams of deionized water was charged to disperse prepolymer. To 50 gm deionized water was charged 9.1 gm of the imidazolidinone diamine of the formula

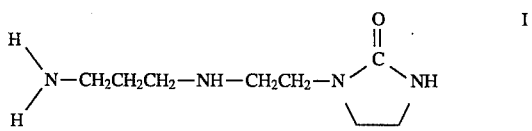
I and this mixture was added to reaction vessel over a 3 minute period. Properties of the dispersion and test results are as follows:

pH=8.9

Viscosity=3,850 mPas

Solids=39.27%

To this dispersion was added 5% by weight Desmodur DA (water dispersible polyfunctional isocyanate). The formulation was then applied to particle board by spraying and dried for 10 minutes. Substrates were vacuum formed using heat and aged 24 hours at ambient room temperature. 180 degree peel results:

peak reading=1409 g/cm valley reading=204 g/cm average peel value=1154 g/cm

The peak and average values are determined by using a slip/peel tester (Model SP-101B, IMASS Inc). The slip/peel tester measures the coefficient of friction between surfaces or peel strengths of adhesives. The test speeds were set at 2 inches (5.08 cm) per minute for 60 seconds.

EXAMPLE 12

Anionic Polyurethane/urea Dispersion

To a reaction flask with efficient stirring and heating was charged 423 gm (0.3021 eq) butane diol adipate polyester polyol, 3.0 gm (0.0671 eq) trimethylolpropane, 19 gm (0.2836 eq) dimethylolpropionic acid, 141 gm (0.1156 eq) meta-tetramethylxylene diisocyanate, and 13.6 gm (0.1344 Moles) triethylamine. The mixture was heated approximately 3 hours at 90° C. When the prepolymer reached 3.5% isocyanate 903.25 gm deionized water was added to disperse. To 50 gm deionized water was charged 27.92 gm of the imidazolidinone diamine of formula I, 5.22 gm monoethanolamine and 2.76 gm diethylenetriamine. This mixture of mono, di, and tri-functional amines were added to the dispersion over a 3 minute period. Physical properties of dispersion and test results are as follows:

pH=7.87

XXIII

Viscosity=3,150 mPas

Solids=40.24%

Particle size: Effective diameter=74 nanometers Mean diameter=63 nanometers

A 2 ml dry film was applied to PVC substrates which were then joined under 50 psi pressure at the temperatures given below for 30 seconds. The loads at which the bond failed when tested under T-peel conditions are given below.

125° F.=284 g/cm

150° F.=618 g/cm

175° F.=1151 g/cm

200° F.=1199 g/cm

EXAMPLE 13

Emulsion Polymerized Imidazolidinone Functional Latex

In a 100 ml round bottom flask was charged 95.10 gm acetone, 50.14 gm Jeffamine® ED-2001 polyethoxylated/propoxylated diamine, 6 gm of the imidazolidinone diamine of formula I and 3 gm allylamine. The mixture was heated and stirred until the ingredients were disolved and then 19.8 gm tetramethylxylenediisocyanate was added slowly. The mixture was then refluxed until isocyanate, as monitored by infrared, had substantially all been consumed. The acetone solvent was then removed by evaporation, yielding an allylic imidazolidinone functional oligomer.

To a two liter flask equipped with stirrer, condenser, nitrogen inlet, temperature controlled water bath and monomer addition pump were charged 236.1 gm of deionizes water. The water bath was heated so as to provide a reaction temperature of 65° C. Five percent of a monomer mixture containing 134.5 gm deionized water, 36.8 gm of 30 mole ethoxylated octylphenol surfactant, 221 gm butyl acrylate, 157.6 gm methyl methacrylate, 5.9 gm methacrylic acid and 42.7 gm of the allylic imidazolidinone functional oligomer of the previous paragraph was charged to the reaction vessel. 1.24 gm each of ammonium persulfate and sodium metabisulfite were then added to the vessel to initiate the polymerization reaction. The remainder of the monomer mixture was added over a three hour period. Meanwhile, additional feeds of 1.29 gm ammonium persulfate in 24 gm deionized water and 1.29 gm sodium metabisulfite in 24 gm deionized water were added to the reactor vessel over a time period of 4 hours. One half hour after the addition of the catalyst was complete, the contents of the reactor were cooled and discharged.

The product was an aqueous latex having a solids content of 46.0%, a pH of 6.0, a particle size of 210 nm, a Brookfield viscosity of 40 mPas, and coagulum content of only 0.1%. The polymer had an intrinsic viscosity of 0.335 and an acetone insoluble content of 61%.

EXAMPLE 14

To a reaction flask fitted with overhead stirrer, thermometer and nitrogen inlet is charged a polyester polyol along with 5% by weight of the imidazolidinone diamine of formula I. The mixture is heated to 85°–90° C. and amine number monitored to determine reaction completion. The product is a polyester/polyamide polyol.

EXAMPLE 15

The imidazolidinone diamine of the formula I was incorporated into a thermoforming water dispersible polyurethane and compared with a control formulation utilizing the same number of equivalents of mono, di, and triamine. The formulations are shown in Table 1.

TABLE 1

| Component Number | Component | Equivalents of active group | |
|---|---|---|---|
| | | Control | Example 15 |
| 1 | Hexanedioic acid/butanediol polyester diol (Rucoflex ™ S-102-40) | 0.3021 | 0.3021 |
| 2 | Trimethylolpropane | 0.0671 | 0.0671 |
| 3 | Dimethylolpropionic acid | 0.2836 | 0.2836 |
| 4 | 1,3-Bis(1-isocyanato-1-methylethyl)-benzene | 1.156 | 1.156 |
| 5 | Monoethanolamine | 0.1245 | 0.0856 |
| 6 | Ethylenediamine | 0.2463 | — |
| 7 | Formula I diamine: | | |
| | Equivalents diamine | — | 0.2463 |
| | Equivalents monoamine | | 0.0389 |
| 8 | Diethylene triamine | 0.0811 | 0.0811 |

The respective formulations were prepared by drying component (1) under vacuum in a clean reactor at 110° C. for 1 hour; adding components (2), (3) and (4) with agitation and holding the temperature at 90° C. for 4 hours (NCO content approximately 3.5%); adding the amines (5)-(8) to a sufficient quantity of deionized water to provide a 39.25% solids formulation when added to the reactor; and then adding the amine/water mixture to the reactor over a 3 minute period. Properties of the respective dispersions were as follows.:

| Control | Example 15 |
|---|---|
| pH = 8.0 | pH = 8.0 |
| Viscosity = 50 mPas | Viscosity = 260 mPas |
| Solids = 39.2% | Solids = 39.3% |
| Mean particle size = 89 nm | Mean particle size = 63 nm |

Heat activating temperatures of the two polymer dispersions were tested on untreated vinyl and results indicated substantially similar heat activating properties. The two dispersions were then tested on ABS/vinyl with 5% Desmodur DA as a polyfunctional isocyanate crosslinker and a heat activation temperature of 50° C. for 20 seconds was applied. After a 24-hour period at room temperature, peel values on both polymers gave vinyl failure. The two dispersions were also tested at 90° C. for 24 hours and results demonstrated that the dispersion employing the invention polymer with imidazolidinone functionality dramatically improved adhesion at these elevated temperatures.

EXAMPLE 16

To a reaction flask was charged 24.2 gm (0.039 Eq) Joncryl 587 which is a hydroxy functional styrene/acrylic copolymer from S.C. Johnson Wax, 225 gm (1.717 Eq) hydrogenated MDI, and 197 gm of n-methyl pyrrolidone. This mixture was heated at 85° C. for 1 hour. To this was charged 24.2 gm (0.361 Eq) dimethylolpropionic acid, 183 gm Rucoflex S-102–110 (a butanediol/adipate polyester polyol). The mixture was heated for 2–3 hours at 85° C. The diamine of formula XVII, 34.5 gm (0.3224 Eq), was slowly added to this mixture over a 15 minute period. Then 17.6 gm (0.174 moles) triethylamine was added and the prepolymer was dispersed in 740 gm (41.1 moles) de-ionized water. To the dispersion was charged a solution containing 3.2 gm (0.094 Eq) diethylene triamine, 11.6 gm (0.386 Eq) ethylene diamine, and 27 gm (1.5 moles) of de-ionized water. The aqueous and dried physical properties of the polymer are described below.

| | |
|---|---|
| Color, wet | Translucent |
| Color, Dry | Clear |
| Solids | 35% |
| Viscosity | 50 cps (mPa · s) |
| Tabor Abrasion (H-18 wheel, 100 cycles, 1 kg weights) | 33.8 mg loss |
| Shore D Hardness (ASTM 2240-75) | 80 |
| Pencil Hardness (ASTM D 3363-74) | 2B |
| Gloss: | |
| 20 Degrees | 92.7% |
| 65 Degrees | 90.3% |
| 85 Degrees | 99.8% |
| Tensile Strength | 1,700 psi |
| Elongation | 180% |
| 3-Day solvent swell (Linear) @ 60° C. | |
| Water | 0% (Clear) |
| Xylenes | 10% (Clear) |
| Skydrol | 40% (Clear) |
| Water/Ethylene glycol (50:50) | 10.5% (Clear) |
| Tg | −50° C. |
| Cahn Dynamic Contact Angle Analyzer: | |
| Wicking rate (water) | 0.0120 mg/sec |
| Dried film surface tension | 35.46 dynes/cm |

EXAMPLE 17

To a reaction flask was charged 300 gm (0.294 Eq) Rucoflex S-1011-55, a diethylene glycol/adipate polyester polyol, 16.2 gm (0.24 Eq) dimethylolpropionic acid, 96 gm TMXDI (.7869 Eq), 12.3 gm (0.121 moles) triethylamine, and 0.14 gm Metacure T-12. The mixture was heated to 80° C. until isocyanate reached 2.3%. The prepolymer was dispersed in 599 gm (33.28 moles) de-ionized water and then slowly a mixture containing 3.15 gm (0.05 Eq) monoethanolamine, 18 gm (0.168 Eq) of the diamine of formula XVII, and 29 gm (1.61 moles) de-ionized water was added. The resulting polymer properties are described below.

pH=8.29

Viscosity=180 cps
Mean diameter particle size=51 nm
Solids=40.57
Dried film=Clear and slightly tacky

EXAMPLE 18

To a reaction flask was charged 271.74 gm hexanediol, 311.31 gm adipic acid, 0.6 gm Fascat 9100, and 16.36 gm of a diamine of formula XVII. The mixture was heated to 210° C. for 3.5 hours while pulling off water. An additional hour pulling off water at 30 inches Hg and 220° C. completes the reaction. The sample, a beige, waxy solid was tested to have an acid number of 0.55 and a hydroxy value at 52.0 (Theoretical=54.87). The melt point using a differential scanning calorimeter was Tm=55.63. GPC weight average and number average molecular weights of high polymers are 7,600 g/mol and 4,280 g/mol.

EXAMPLE 19

Wet adhesion monomer (WAM) synthesis
The following components were charged to a three neck round bottom flask, equipped with a thermometer and a magnetic stirring bar.

| Components | Grams |
| --- | --- |
| Methyl methacrylate | 50.0 |
| Methacrylic Anhydride | 3.0 |
| Diamine of formula XVII | 3.91 |
| P-Toluene Sulfonic Acid | 2.91 (65% active) |

Methyl methacrylate and methacrylic anhydride were mixed; then the diamine of formula XVII was added slowly, keeping the temperature below 35° C. The disappearance of anhydride was monitored by IR Spectroscopy. Once the anhydride was consumed, the secondary amine was neutralized with the sulfonic acid. Other acids like acetic acid, formic acid, hydrochloric acid, and sulfuric acid may also be used.

| Components | Amount (grams) |
| --- | --- |
| Reactor Charge | |
| Deionized Water | 370.0 |
| Triton X-200 | 6.8 (Union Carbide Chemical) |
| Glacial Acrylic Acid | 6.1 |
| Ammonia Hydroxide | 6.1 |
| Initiators | |
| Potassium Persulfate | 2.0 |
| Tert butyl hydroperoxide | 0.20 |
| Hydrosulfite | 0.14 |
| Tert butyl hydroperoxide | 0.20 |
| Hydrosulfite | 0.14 |
| Surfactants, Defoamers, and Antimicrobials | |
| Triton X-200 | 6.8 |
| Bubble Breaker 748 | 0.14 (Witco Corporation) |
| Proxel GXL Antimicrobial | 1.5 (Dow Corning) |
| Monomer Charge | |
| N-butyl acrylate | 218 |
| Methyl methacrylate | 211 |
| methacrylic acid | 1.0 |

Pre-emulsion synthesis
A reactor was charged with 74g water, 6.8g Triton X-200, and mixed for 15 minutes to disperse. With good agitation, N-butyl acrylate, methyl methacrylate, the wet adhesion monomer mixture described above, and methacrylic acid were charged respectively over a 30 minutes period.
Polymerization To a reactor was charged water, Triton X-200, and acrylic acid. Adjust pH to 7–8 with ammonium hydroxide. The bubble breaker 748 was added and the contents heated to 80° C. Two percent of the pre-emulsion synthesis mixture was charged with the potassium persulfate catalyst and then the mixture was held for 15 minutes. The pre-emulsion mixture was then fed uniformly over a three hour period. The mixture was held an extra 30 minutes after the pre-emulsion addition was complete. Then the first treat of t-butyl hydroperoxide was added, followed by hydrosulfite. The mixture was held 10 minutes then the second peroxide treat added and the mixture heated an additional 30 minutes. The reaction mixture was then cooled below 30° C. and the Proxel GXL was added. The pH was adjusted to 9.5 with ammonium hydroxide.

Properties of the resulting polymer dispersion are described below:
pH=9.5
Viscosity=60 centipoise
Particle size=230 run

EXAMPLE 20

Example 19 was repeated with a wet adhesion monomer synthesized with a monofunctional isocyanate.
WAM synthesis
To a three neck round bottom flask, equipped with a thermometer and a magnetic stirring bar, were charged the following components:

| Components | Amount (grams) |
| --- | --- |
| Methyl methacrylate | 50.0 |
| Methacrylic Anhydride | 3.0 |
| Diamine of formula XVII | 3.91 |
| Phenyl isocyanate | 2.1 |

Methyl methacrylate and methacrylic anhydride were mixed together. Diamine of formula XVII was added slowly keeping the temperature below 30 Deg °C. The reaction was monitored by IR spectroscopy and was complete with the disappearance of anhydride. To this mixture was slowly added phenyl isocyanate and monitored by IR.

Properties of latex obtained are described below.
pH=9.8
Viscosity=1,800 cps
Solids=51.77%
Particle size (Mean diameter)=208 nanometer, monomodal

EXAMPLE 21

Polymer synthesis was repeated as described in example 19 except the wet adhesion monomer composition was varied.
WAM synthesis
A three neck round bottom flask, equipped with a thermometer and magnetic stirring, was charged with the following components:

| Components | Amount (grams) |
|---|---|
| Methyl methacrylate | 50.0 |
| Methacrylic Anhydride | 3.0 |
| Diamine of formula XVII | 3.91 |
| Cyclohexyl isocyanate | 2.1 |

Methyl methacrylate and methacrylic anhydride were blended together then Diamine of formula XVII was slowly added over a 5 minute period keeping the temperature below 35° C. To this was slowly added cyclohexyl isocyanate keeping the temperature below 35° C.

This latex's properties are described below.

pH=9.3

Viscosity=80 centipoise

Solids=51.83%

Particle size (Mean diameter)=306 nm

The monomer synthesis described above is the process of choice. The imidazolidinone diamine is modified in a reactive diluent eliminating the use of organic solvents. The WAM monomers generated using this process were easily synthesized in a one batch process.

EXAMPLE 22

A latex was formulated into a semi-gloss paint and tested for wet adhesion characteristics.

| Components | Amount (grams) |
|---|---|
| Wet adhesion monomer | |
| Methyl methacrylate | 50.0 |
| Methacrylic anhydride | 3.0 |
| Diamine of formula XVII | 3.91 |
| Phenyl isocyanate | 2.1 |
| Reactor charge | |
| Deionized water | 370.0 |
| Triton X-200 | 6.8 |
| Glacial acrylic Acid | 6.1 |
| Ammonia hydroxide | 6.1 |
| Initiators | |
| Potassium persulfate | 2.0 |
| t-butyl hydroperoxide | (0.20) × 2 |
| Hydrosulfite | (0.14) × 2 |
| Monomer Charge | |
| n-Butyl acrylate | 218.0 |
| Methyl methacrylate | 211.0 |
| Methacrylic acid | 1.0 |
| Surfactants, Defoamers, and Antimicrobials | |
| Triton X-200 | 6.8 |
| Bubble breaker 748 | 0.14 |
| Proxel GXL antimicrobial | 1.5 |

This latex was formulated into a semi-gloss paint.

| Components | Amount (grams) |
|---|---|
| Pigment grind | |
| Water | 66.6 |
| Colloid 226/35 (Rhone-Poulenc) | 6.2 |
| Nuosept 95 (Huls America) | 1.5 |
| AMP-95 (Angus Chemical) | 1.5 |
| Polyphase AF-1 (Troy Chemical) | 4.0 |
| Igepal CO-630 (Rhone-Poulenc) | 3.5 |
| Tiona RCL-2 (SCM Chemicals) | 250.0 |
| Atomite (ECC America) | 20.0 |
| ASP-170 (Englehard Corporation) | 30.0 |
| Drewplus L-464 (Drew Industries) | 1.8 |
| Letdown | |
| Water | 218.4 |
| Latex described above | 400.5 |
| Propylene Glycol | 47.6 |
| Texanol (Eastman Chemical) | 15.1 |
| Rheolate 278 (Rheox, Inc.) | 7.0 |
| Natrosol 250 MHBR (Aqualon Company) | 2.7 |
| Drewplus L-464 | 3.7 |

The paint (1.5 grams) described above was brushed onto an alkyd resin coated board, covered with cheese cloth, then coated again with paint(4.9 grams). This was dried at ambient room temperature for 7 days. The painted substrate was soaked in water for 1 hour and tested on an Intellect®500 for 180° peel adhesion. This sample had a wet adhesion peel value of 7.2 kilograms/linear inch.

EXAMPLE 23

To a reaction vessel was charged 345 gm (0.6765 Eq) butanediol adipate polyester polyol, 37.1 gm (0.5537 Eq) dimethylolproprionic acid, 320 gm (2.62 Eq) tetramethylxylene diisocyanate (TMXDI) and 26.5 gm (0.262 moles) triethylamine. This mixture was heated at 80° C. until percent isocyanate was 8.0. The prepolymer was dispersed in 1,254 gm de-ionized water and to this was charged a mixture containing 134 gm (1.25 Eq) of the diamine of example 6 in 275 gm deionized water. The resulting polymer dispersion properties are described below.

pH=7.6

Viscosity=80 centipoise

Mean Particle size=59 nanometers

Solids=36.6%

Dried film=Clear

What is claimed is:

1. A free-radically polymerizable monomer or prepolymer compound comprising a free-radically polymerizable ethylenically unsaturated group and a group of the formula:

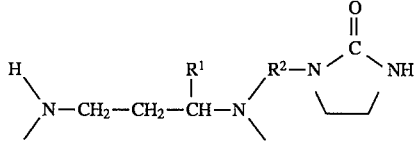

where $R^1$ is H, or a $C_1$–$C_{17}$ alkyl group, and $R^2$ is a $C_1$–$C_{20}$ alkylene group optionally interrupted with one or more ether oxygen atoms.

2. A compound as in claim 1 wherein $R^1$ is methyl or ethyl and $R^2$ is ethylene or propyleneoxyethylene.

3. A compound as in claim 1 prepared by reaction of:

a) a plural isocyanate or epoxy functional compound, b) an ethylenically unsaturated compound having an active hydrogen functional group, and c) a compound of the formula:

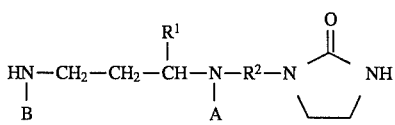

where A is H or a residue of an isocyanate, isothiocyanate, epoxy, carbonate, carboxylic or sulfonic acid, anhydride, chloroformate, ester, or alkyl halide compound, B is defined as for A and is the same as or different than A, at least one of A and B is H, $R^1$ is H, or a $C_1$–$C_{17}$ alkyl group and $R^2$, is $C_1$–$C_{20}$ alkylene optionally interrupted with one or more ether oxygen atoms.

4. A compound as in claim 3 wherein said ethylenically unsaturated compound (b) is selected from the group consisting of allyl alcohol, allyl amine, acrylic acid, hydroxyethyl acrylate, hydroxypropyl acrylate, diethylene glycol monoacrylate, triethylene glycol monoacrylate, polyethylene glycol monoacrylate, hydroxyethyl methacrylate, hydroxypropyl methacrylate, diethylene glycol monomethacrylate, triethylene glycol monomethacrylate, polyethylene glycol monomethacrylate, crotonic acid, itaconic acid, maleic acid, fumaric acid and half esters of maleic and fumaric acids.

5. A compound as in claim 1 prepared by reaction of:
a) an ethylenically unsaturated acid, acid chloride, anhydride, isocyanate, isothiocyanate, ester, or epoxy compound, and
b) a compound of the formula:

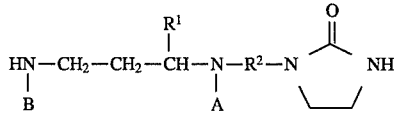

where A is H or a residue of an isocyanate, isothiocyanate, epoxy, carbonate, carboxylic or sulfonic acid, anhydride, chloroformate, ester, or alkyl halide compound, B is defined as for A and is the same as or different than A, at least one of A and B is H, $R^1$ is H, or a $C_1$–$C_{17}$ alkyl group and $R^2$ is $C_1$–$C_{20}$ alkylene optionally interrupted with one or more ether oxygen atoms.

6. A compound as in claim 5 wherein said ethylenically unsaturated compound (a) is selected from the group consisting of acrylic and methacrylic acids and their anhydrides and acid chlorides, isocyanatoethyl methacrylate, isocyanatoethyl acrylate, glycidyl acrylate, glycidyl methacrylate, vinyl glycidyl ether and a mono-, di-, or triisocyanate of the formula:

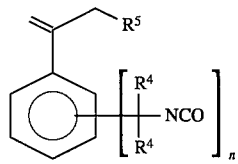

where each $R^4$ is independently a $C_{1-6}$ alkyl, $R^5$ is H or $R^4$ and n is 1–3.

7. A compound as in claim 1 wherein $R^1$ is H, methyl or ethyl.

* * * * *

UNITED STATES PATENT AND TRADEMARK OFFICE
CERTIFICATE OF CORRECTION

PATENT NO. : 5,496,907
DATED : March 5, 1996
INVENTOR(S) : MICHAEL DOCHNIAK

It is certified that error appears in the above-identified patent and that said Letters Patent is hereby corrected as shown below:

Col. 13, line 41, insert LATEX SYNTHESIS on top of the line, over the word "components";

Col. 14, line 62, delete "i9" and insert -- 19 --;

Signed and Sealed this

Twentieth Day of August, 1996

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,496,907

DATED : March 5, 1996

INVENTOR(S) : MICHAEL J. DOCHNIAK

It is certified that error appears in the above-identified patent and that said Letters Patent is hereby corrected as shown below:

Col. 2, line 10, delete "sane" and insert -- same --;

Col. 3, line 52, delete "!II" and insert -- III --;

Col. 7, line 34, delete "tool" and insert -- mol --;

Signed and Sealed this

Twenty-fourth Day of September, 1996

Attest:

BRUCE LEHMAN

Attesting Officer     Commissioner of Patents and Trademarks